US007575552B2

(12) United States Patent
Saito

(10) Patent No.: US 7,575,552 B2
(45) Date of Patent: Aug. 18, 2009

(54) ULTRASONIC PROBE WITH ACOUSTIC MEDIUM

(75) Inventor: Koetsu Saito, Nakano-ku (JP)

(73) Assignee: Panasonic Corporation, Osaka (JP)

( * ) Notice: Subject to any disclaimer, the term of this patent is extended or adjusted under 35 U.S.C. 154(b) by 254 days.

(21) Appl. No.: 10/559,881

(22) PCT Filed: May 19, 2005

(86) PCT No.: PCT/JP2005/009121

§ 371 (c)(1),
(2), (4) Date: Dec. 7, 2005

(87) PCT Pub. No.: WO2005/120356

PCT Pub. Date: Dec. 22, 2005

(65) Prior Publication Data

US 2007/0112271 A1 May 17, 2007

(30) Foreign Application Priority Data

Jun. 10, 2004 (JP) ............................ 2004-172231

(51) Int. Cl.
*A61B 8/00* (2006.01)

(52) U.S. Cl. ...................................... 600/459; 600/437

(58) Field of Classification Search .................. 604/20; 600/437

See application file for complete search history.

(56) References Cited

U.S. PATENT DOCUMENTS

| | | | | |
|---|---|---|---|---|
| 4,494,548 | A * | 1/1985 | Buon et al. | 600/446 |
| 5,460,179 | A * | 10/1995 | Okunuki et al. | 600/444 |
| 5,722,397 | A * | 3/1998 | Eppstein | 600/345 |
| 7,001,355 | B2 * | 2/2006 | Nunomura et al. | 604/22 |
| 2001/0041856 | A1 * | 11/2001 | McDaniel | 604/22 |
| 2002/0055702 | A1 * | 5/2002 | Atala et al. | 604/20 |
| 2003/0190336 | A1 * | 10/2003 | Adams et al. | 424/401 |
| 2003/0229283 | A1 | 12/2003 | Craig et al. | |
| 2004/0010222 | A1 * | 1/2004 | Nunomura et al. | 604/22 |
| 2005/0154239 | A1 * | 7/2005 | Windhorst et al. | 568/863 |

FOREIGN PATENT DOCUMENTS

| | | |
|---|---|---|
| EP | 0 174 167 | 3/1986 |
| EP | 0 455 273 | 11/1991 |

(Continued)

OTHER PUBLICATIONS

Hawrylak, Brent et al. Ultrasonic Velocity an Volumetric Properties of Isomeric Butanediols Plus Water Systems. Can. J. Chem, 1998: 76 (464-468).*

(Continued)

*Primary Examiner*—Eric F Winakur
*Assistant Examiner*—Helene Bor
(74) *Attorney, Agent, or Firm*—Hamre, Schumann, Mueller & Larson, P.C.

(57) ABSTRACT

There is provided an ultrasonic probe that can transmit and receive ultrasonic waves with high sensitivity and can drive an ultrasonic transducing part smoothly at high speed. The ultrasonic probe according to the present invention includes: an ultrasonic transducing part 101 for transmitting and receiving an ultrasonic wave; an outer case 105 for storing the ultrasonic transducing part 101; and an acoustic medium 106 charged in the outer case 105, wherein the acoustic medium 106 contains 1,2-butylene glycol.

8 Claims, 4 Drawing Sheets

FOREIGN PATENT DOCUMENTS

| | | | |
|---|---|---|---|
| JP | 61-58647 | | 3/1986 |
| JP | 61149128 | * | 7/1986 |
| JP | 3-32652 | | 2/1991 |
| JP | 4-84946 | | 3/1992 |
| JP | 4-322642 | | 11/1992 |
| JP | 2001-178727 | | 7/2001 |
| JP | 2002-85403 | | 3/2002 |

OTHER PUBLICATIONS

Hawrylak, Brent et al. Viscosity, Surface Tension, and Refractive Index Measurements of Mixtures of Isomeric Butanediols with Water. Journal of Solution Chemistry, 1998: vol. 27, No. 9 (827-841).*

Ludwig, George. The Velocity of Sound through Tissues and the Acoustic Impedance of Tissues. The Journal of the Acoustical Society of America, Nov. 1950: (22)(6) 862-866.*

Schafer, Mark E et al. Use of Time Delay Spectrometry in Fluid Attenuation Measurement Ultrasonics Symposium, 1989: 973-976.*

Anderson, Bonita. Echocardiography: The Normal Examination and Echocardiographic Measurements. Chapter 1: Basic Principles of Two-Dimensional Ultrasound Imaging, p. 4. Blackwell Publishing, 2000. [ISBN 0646391399, 9780646391397].*

* cited by examiner

ULTRASONIC PROBE WITH ACOUSTIC MEDIUM

TECHNICAL FIELD

The present invention relates to an ultrasonic probe for use in an ultrasonic diagnostic apparatus or the like.

BACKGROUND ART

A known ultrasonic probe used in an ultrasonic diagnostic apparatus performs ultrasonic scanning by mechanically oscillating or rotating an ultrasonic transducing part for transmitting and receiving ultrasonic waves in an outer case filled with an acoustic medium. In such an ultrasonic probe, a material having an acoustic impedance similar to that of a living body, specifically a liquid such as liquid paraffin, is used as the acoustic medium (for example, Patent Documents 1 to 3).

Patent Document 1: JP 2001-178727 A

Patent Document 2: JP 3(1991)-32652 A

Patent Document 3: JP 4(1992)-84946 A

DISCLOSURE OF INVENTION

Problem to be Solved by the Invention

However, in the conventional ultrasonic probe, although the material such as liquid paraffin used as the acoustic medium has an acoustic impedance similar to that of a living body, there is a problem in acoustic characteristics, such as strong ultrasonic attenuation, for example. Consequently, the transmitting/receiving sensitivity for ultrasonic waves is degraded, resulting in a decrease in the quality of an ultrasonic image. Moreover, due to the high viscosity of the above-mentioned acoustic medium, a high load torque is applied to a motor when the ultrasonic transducing part is oscillated or rotated mechanically by the rotor and the like in this medium, which makes it difficult to drive the ultrasonic transducing part smoothly at high speed.

It is an object of the present invention to provide an ultrasonic probe that can transmit and receive ultrasonic waves with high sensitivity and can drive the ultrasonic transducing part smoothly at high speed.

Means for Solving Problem

In order to achieve the above-mentioned object, an ultrasonic probe according to the present invention includes: an ultrasonic transducing part for transmitting and receiving an ultrasonic wave; an outer case for storing the ultrasonic transducing part; and an acoustic medium charged in the outer case, wherein the acoustic medium contains 1,2-butylene glycol.

EFFECTS OF THE INVENTION

In the ultrasonic probe according to the present invention, 1,2-butylene glycol is used as the acoustic medium. 1,2-butylene glycol has an acoustic impedance similar to that of a living body, and produces relatively small ultrasonic attenuation. Thus, by using this material as the acoustic medium, it becomes possible to transmit and receive ultrasonic waves with high sensitivity. In addition, 1,2-butylene glycol has a relatively low viscosity. Thus, by using this material as the acoustic medium, it becomes possible to drive the ultrasonic transducing part smoothly at high speed.

DESCRIPTION OF THE INVENTION

As mentioned above, the ultrasonic probe according to the present invention includes: an ultrasonic transducing part for transmitting and receiving an ultrasonic wave; an outer case for storing the ultrasonic transducing part; and an acoustic medium charged in the outer case. The ultrasonic probe may be a mechanical scanning type ultrasonic probe that includes a mechanism for oscillating or rotating the ultrasonic transducing part. Further, the ultrasonic probe may be an electronic scanning type ultrasonic probe in which the ultrasonic transducing part includes an array element in which a plurality of transducers are arranged.

As the acoustic medium, 1,2-butylene glycol is used. 1,2-butylene glycol may be used singly, but also can be used in combination with other materials.

The content of 1,2-butylene glycol in the acoustic medium is not particularly limited, and is changed depending on a material to be combined. Preferably, the acoustic medium contains 25 to 100 wt % of 1,2-butylene glycol.

In the ultrasonic probe, the acoustic medium preferably has the characteristics shown below. In particular, when 1,2-butylene glycol is used in combination with other materials as the acoustic medium, it is preferable that the type and the ratio of the material to be combined are adjusted so that the acoustic medium satisfies the following characteristics.

It is preferable that the acoustic medium has an acoustic impedance of 1.4 to 1.6 MRayl, which is similar to that of a living body as a subject, at a temperature of 20° C. An acoustic impedance of 1.45 to 1.517 MRayl is further preferable.

It is preferable that attenuation produced by the acoustic medium at a frequency of 3 MHz is as small in amount as possible and is 0.07 to 0.091 dB/mm.

In the acoustic medium, a material that can propagate ultrasonic waves, is soluble in 1,2-butylene glycol (in other words, no phase separation occurs in a mixture of this material and 1,2-butylene glycol), and a liquid at a temperature of 10° C. to 40° C. can be used in combination with 1,2-butylene glycol. Further, this material preferably has only a small effect (corrosion and the like, for example) on the components (metal, plastics, and the like) of the probe, and is non-toxic or essentially non-toxic to a living body.

Examples of such a material include various types of glycols, water, and the like. In particular, glycols are preferable. Examples of such glycols include 1,3-butylene glycol, ethylene glycol, and the like.

Hereinafter, preferred embodiments of the present invention will be described in more detail with reference to the drawings.

Embodiment 1

Figure 1:
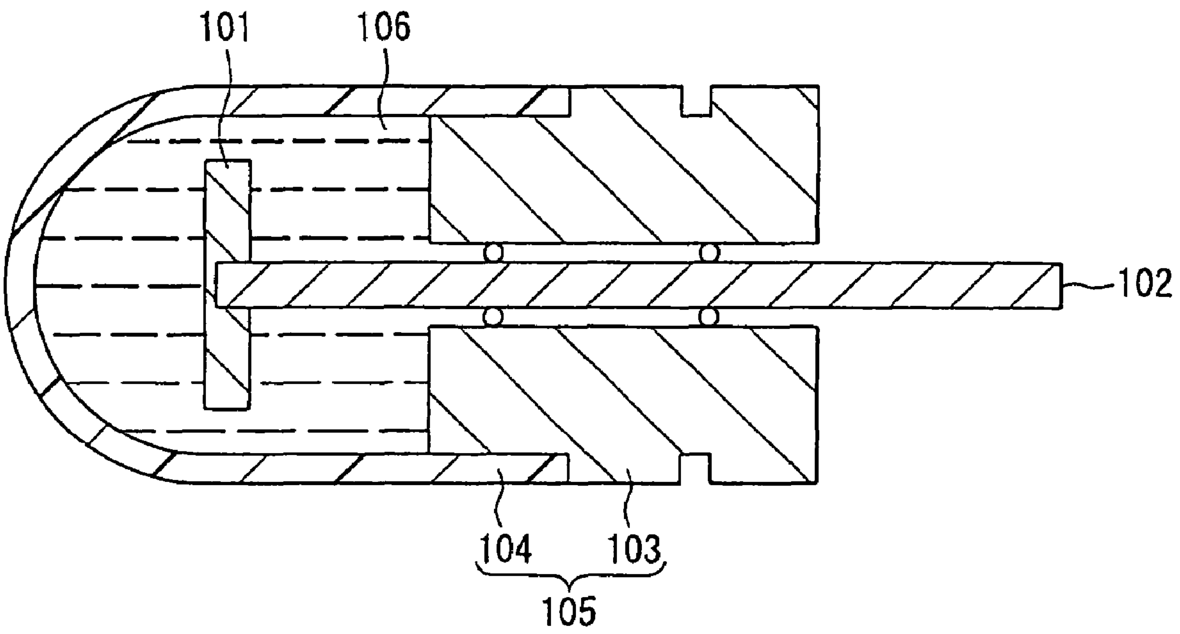
FIG. 1 is a cross-sectional view showing an exemplary ultrasonic probe according to the present invention.

FIG. 1 is a cross-sectional view showing a configuration of an exemplary ultrasonic probe according to the present invention. In this ultrasonic probe, an outer case 105 is constituted by a frame 103 and a window 104 connected to each other, and is charged with a deaerated acoustic medium 106. Further, the outer case 105 stores an ultrasonic transducing part 101 therein. Constituent materials of the window 104 and the acoustic medium 106 will be described in detail later.

The ultrasonic transducing part 101 includes an ultrasonic transducer for transmitting and receiving ultrasonic waves. As the ultrasonic transducer, a piezoelectric material such as a PZT-based piezoelectric ceramic or the like, a polymeric material, a single crystal, or the like is used, for example. On a front surface (surface for transmitting and receiving ultrasonic waves) of the ultrasonic transducer, an acoustic matching layer for transmitting and receiving ultrasonic waves efficiently, and an acoustic lens for converging ultrasonic waves may be provided, if necessary. On a back surface (surface opposite to the surface for transmitting and receiving ultrasonic waves) of the ultrasonic transducer, a backing layer for absorbing ultrasonic waves may be provided.

The ultrasonic transducer is attached to a rotor, whereby the ultrasonic transducing part 101 is configured. The rotor is connected with a drive shaft 102, and further with a driving unit (such as a motor, for example: not shown) for producing a rotating force via the drive shaft 102. With this configuration, a rotating force output from the driving unit is transmitted to the rotor via the drive shaft 102 so as to rotate or oscillate the ultrasonic transducer.

Next, an operation of the ultrasonic probe will be described. The ultrasonic probe is connected to an ultrasonic diagnostic apparatus in use. The ultrasonic diagnostic apparatus includes, for example, a control part for driving the probe, a transducing part for transmitting and receiving signals to and from the probe, an image formation part for creating an image of an object based on the received signals, and an image display part for displaying a created tomogram.

In ultrasonic diagnosis, initially the ultrasonic probe is placed on a surface of a living body as a subject. At this time, the window 104 is disposed so as to be in direct contact with the living body or in indirect contact therewith via an ultrasonic propagation medium. The driving unit of the probe is driven by a driving signal from the control part of the ultrasonic diagnostic apparatus, so as to rotate or oscillate the ultrasonic transducing part 101. Then, an electric signal (transmission signal) is transmitted from the transducing part of the ultrasonic diagnostic apparatus to the ultrasonic probe. The transmission signal is converted into an ultrasonic wave by the ultrasonic transducing part of the probe, and the converted ultrasonic wave is propagated through the acoustic medium 106 and the window 104 to the living body. This ultrasonic wave is reflected by a target in the living body. The ultrasonic transducing part 101 of the probe receives a part of the reflected wave, converts the same into an electric signal (reception signal), and transmits the reception signal to the transducing part of the ultrasonic diagnostic apparatus. This transmitting and receiving operation is performed repeatedly while the ultrasonic transducing part 101 is rotated or oscillated, thereby performing ultrasonic scanning. The reception signal is subjected to processing such as amplification, detection, and the like, and then is output to the image formation part. The image formation part creates an ultrasonic image (tomogram or the like) of the target based on the reception signal, and outputs the created image to the image display part.

As described above, in the ultrasonic probe, a propagation path for the ultrasonic waves includes the acoustic medium 106 in contact with the ultrasonic transducing part 101 and the window 104 containing the acoustic medium 106. The acoustic characteristics, particularly the acoustic impedance and ultrasonic attenuation of the acoustic medium 106 and the window 104 serving as a propagation path of ultrasonic waves, are the key to obtaining an ultrasonic image with high resolution. More specifically, it is preferable that the acoustic medium 106 and the window 104 reflect ultrasonic waves less due to a difference in acoustic impedance between the acoustic medium 106 as well as the window 104 and a subject (a living body, for example), and in other words the acoustic medium 106 and the window 104 have an acoustic impedance similar to the acoustic impedance (1.5 to 1.6 MRayl in the case of a living body, for example) of the subject. Further, in order to suppress degradation in transmitting/receiving sensitivity for ultrasonic waves and frequency characteristics due to attenuation, it is preferable that ultrasonic attenuation is as small in amount as possible. In particular, in view of the existence of frequency-dependent attenuation, this characteristic is crucially important when the ultrasonic transducing part is used with a high frequency so as to obtain a high-resolution image.

Further, in addition to having the above-mentioned acoustic characteristics, the window 104 preferably is less deformed by an external pressure such as pressing against the surface of the subject, so as to oscillate or rotate the ultrasonic transducing part 101 smoothly. In view of this, as the window, a plastic material such as polyethylene, polymethylpentene, and the like can be used, for example. The thickness of the window is not particularly limited, but can be set to about 1 to 3 mm, for example.

In addition to the above-mentioned acoustic characteristics, the acoustic medium 106 preferably has a small viscosity. With a small viscosity, a load (torque and the like) put on the driving unit for driving the drive shaft 102 can be reduced, so that the ultrasonic transducing part 101 can be oscillated or rotated smoothly at high speed. In the case where the subject is a living body, the acoustic medium 106 may flow outward during diagnosis because of some factors and come in contact with the living body. In view of this, the acoustic medium 106 preferably is non-toxic or essentially non-toxic to a living body. In addition, the acoustic medium 106 preferably has no or a small adverse effect (corrosion and the like) on the members being in contact with the acoustic medium, such as the ultrasonic transducing part 101, the drive shaft 102, and the like provided in the outer case 105.

In the present embodiment, only 1,2-butylene glycol is used as the acoustic medium 106, for example.

The acoustic characteristics (the acoustic impedance, the sound velocity, attenuation) of 1,2-butylene glycol have not been revealed. The present inventors evaluated the acoustic characteristics of 1,2-butylene glycol. As a result, it has been found that 1,2-butylene glycol has highly useful characteristics as the acoustic medium as compared with a conventional acoustic medium or other types of butylene glycol as described below. The usefulness of 1,2-butylene glycol as the acoustic medium has been found for the first time by the present inventors.

The following description is directed to the result of evaluating the characteristics of 1,2-butylene glycol.

(1) Acoustic Impedance

The sound velocity of 1,2-butylene glycol was measured to be 1.47 km/s at a temperature of 25° C. and 1.45 km/s at a temperature of 20° C. The measurement of the sound velocity was performed in the following manner. That is, an ultrasonic transducer for transmission and an ultrasonic transducer for reception were provided at a certain distance in a temperature-controlled acoustic medium. A pulse signal was applied to the transducer for transmission, so that ultrasonic waves were propagated through the acoustic medium to be received by the transducer for reception. The time taken for the propagation of the ultrasonic waves was measured. The sound velocity was calculated from the propagation time and the distance between the transducers for transmission and for reception.

It is well known that 1,2-butylene glycol has a density of 1.0 kg/m$^3$ (see, for example, CAS No. 584-03-2 (CHEM EXPER)).

From the above-mentioned values, the acoustic impedance of 1,2-butylene glycol was calculated to be 1.47 MRayl at a temperature of 25° C. and 1.45 MRayl at a temperature of 20° C., which were similar to the acoustic impedance of a living body.

The acoustic impedance of liquid paraffin, castor oil, and 1,3-butylene glycol, which have been proposed as an acoustic medium in a conventional ultrasonic probe, is about 1.19 MRayl, 1.46 MRayl, and 1.54 MRayl, respectively (see Ultrasonic Technique Handbook (Nikkankogyo Shimbun Ltd.)).

(2) Acoustic Attenuation

Figure 2:
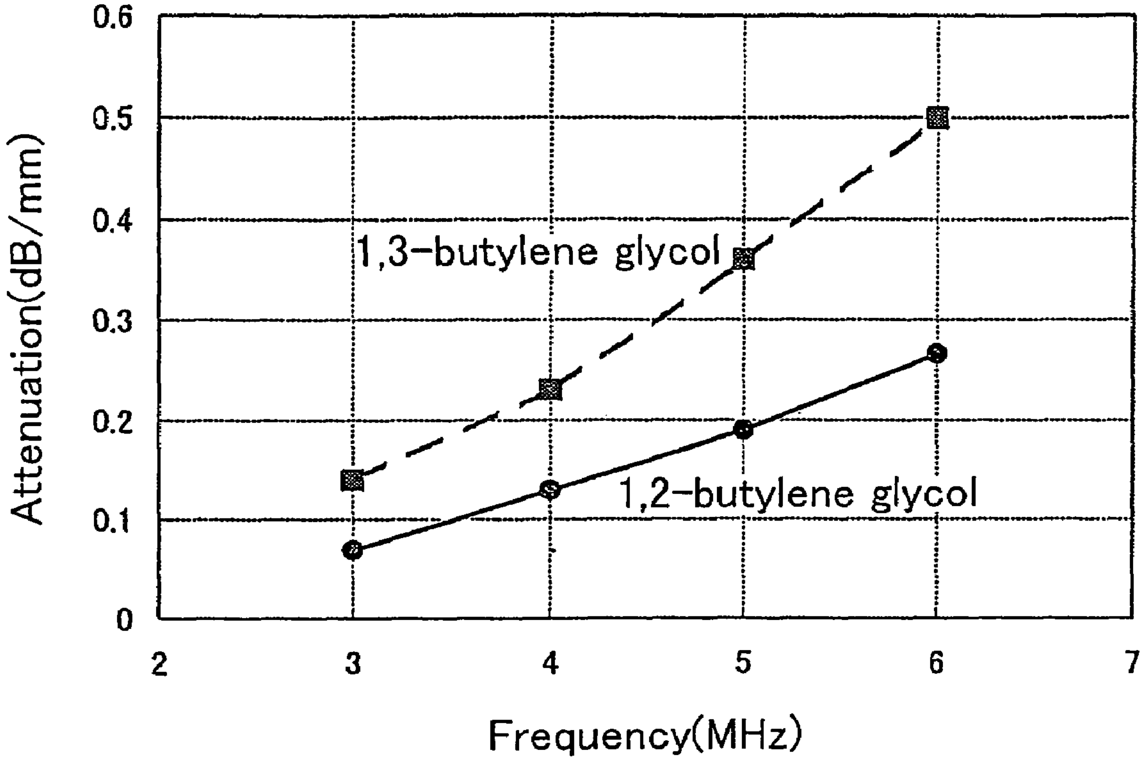
FIG. 2 is a graph showing the ultrasonic attenuation characteristics of 1,2-butylene glycol and 1,3-butylene glycol with respect to respective frequencies.

Ultrasonic attenuation of 1,2-butylene glycol at respective frequencies was measured. Also, ultrasonic attenuation of 1,3-butylene glycol was measured as a comparative example. The results are shown in FIG. 2. The measurement of ultrasonic attenuation was performed in the following manner. That is, by using the same system as that used for the measurement of the sound velocity, about 30 sin-waves of an arbitrary frequency were applied to the transducer for transmission, ultrasonic waves propagated through the acoustic medium were received by the transducer for reception, and a reception voltage was measured. Further, the transducers for transmission and for reception were moved by a certain distance (10 mm, for example), and a reception voltage was measured in the same manner. Ultrasonic attenuation was calculated from the ratio between the reception voltages and the distance of the transducers for transmission and for reception.

As shown in FIG. 2, it was confirmed that ultrasonic attenuation produced by 1,2-butylene glycol was small in amount as compared with 1,3-butylene glycol. For example, at a frequency of 3 MHz, 1,2-butylene glycol produced an attenuation of 0.07 dB/mm, while 1,3-butylene glycol produced an attenuation of 0.14 dB/mm. As above, the amount of attenuation of 1,2-butylene glycol was about half of that of 1,3-butylene glycol. Further, it was confirmed that the difference in the amount of attenuation increased with frequency.

(3) Viscosity

Figure 3:
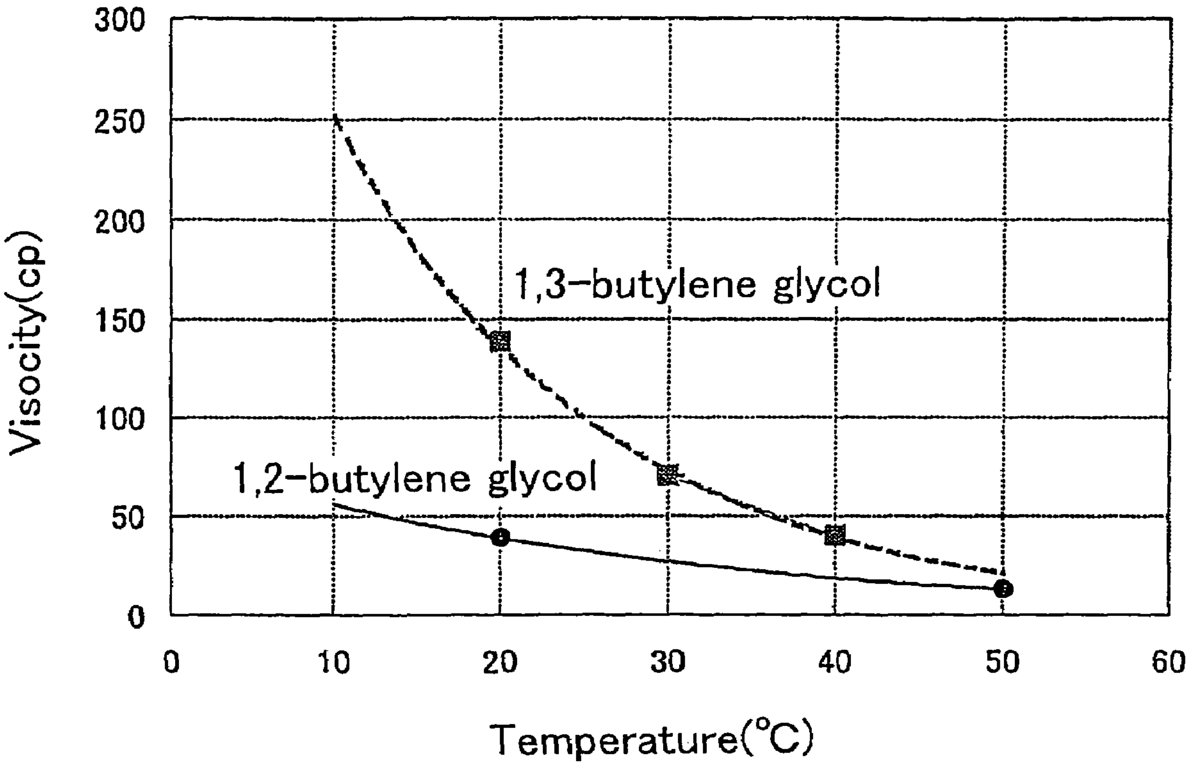
FIG. 3 is a graph showing the viscosities of 1,2-butylene glycol and 1,3-butylene glycol at respective temperatures.

FIG. 3 is a graph showing the temperature characteristics with respect to the viscosity of 1,2-butylene glycol. FIG. 3 also shows the temperature characteristics with respect to the viscosity of 1,3-butylene glycol as a comparative example.

As is evident from FIG. 3, it was confirmed that 1,2-butylene glycol had an extremely low viscosity as compared with 1,3-butylene glycol. For example, in a range of 10° C. to 40° C. (range of an environmental temperature of ordinary use of the probe), there was a clear difference in viscosity. In particular, at a low temperature of 10° C., the viscosity of 1,2-butylene glycol was not more than about quarter of that of 1,3-butylene glycol. The viscosity at this time was almost the same in level as that of 1,3-butylene glycol obtained at a temperature of about 37° C. Since the viscosity of castor oil is 986 cp at 20° C., 1,2-butylene glycol also has an extremely low viscosity as compared with castor oil.

(4) Other Characteristics 1,2-butylene glycol is a material having only a very small effect on a living body. Also, this material has only a very small adverse effect, such as corrosion, on the components such as the window formed of a plastic or the like, the ultrasonic transducing part formed of a piezoelectric ceramic or the like, and the drive shaft and the frame formed of metal or the like.

As described above, it was confirmed that 1,2-butylene glycol had favorable characteristics as the acoustic medium in terms of the acoustic characteristics, the viscosity, an effect (safety) on a living body, and an effect on the components. Consequently, by using 1,2-butylene glycol as the acoustic medium, an ultrasonic probe with high performance, high quality, and safety can be obtained.

In particular, since 1,2-butylene glycol produces a small amount of ultrasonic attenuation, it is possible to improve the transmitting/receiving sensitivity for ultrasonic waves. Moreover, due to a low level of frequency-dependent attenuation, transmission and reception can be performed at a high frequency, whereby it becomes possible to carry out ultrasonic diagnosis with high resolution and high sensitivity. Further, since 1,2-butylene glycol has a low viscosity, it is possible to reduce a load put on a motor due to viscous drag of the acoustic medium when the ultrasonic transducing part is oscillated or rotated for scanning. Consequently, the ultrasonic transducing part can be driven smoothly (constant speed driving or the like, for example) at high speed. Further, it is possible to achieve a reduction in the size of a motor and in driving current.

The above description has been given taking as an example the case of using mechanical scanning in which the transducer is rotated by a motor. However, it is also possible to use electronic scanning by an array element in which a plurality of transducers are arranged in a strip shape.

Embodiment 2

In Embodiment 1, the description has been given of the case where only 1,2-butylene glycol is used as the acoustic medium. However, the present invention is not limited thereto, and 1,2-butylene glycol may be used in combination with other materials. In the present embodiment, a description will be given of the case where a mixture of 1,2-butylene glycol and 1,3-butylene glycol is used as an example of the acoustic medium.

An ultrasonic probe according to the present embodiment has the same configuration as that in Embodiment 1 except for the composition of the acoustic medium, and is operated in the same manner as in Embodiment 1.

(1) Acoustic Impedance

Figure 4:
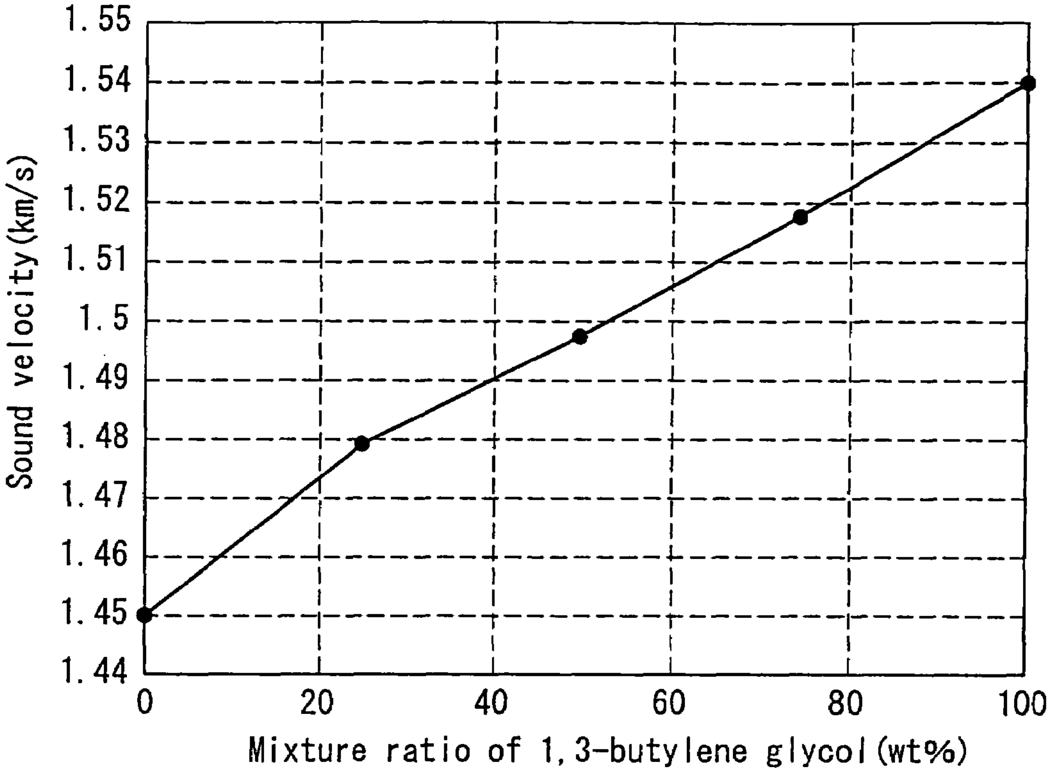
FIG. 4 is a graph showing the relationship between a mixture ratio and a sound velocity with respect to a mixture of 1,2-butylene glycol and 1,3-butylene glycol.

FIG. 4 is a graph showing the result of measuring the sound velocity of the mixture of 1,2-butylene glycol and 1,3-butylene glycol when the mixture ratio (weight ratio) thereof is changed. The measurement of the sound velocity was performed in the same manner as described above, and the temperature was 25° C.

In FIG. 4, a horizontal axis represents a mixture ratio, indicating that the mixture contains a larger amount of 1,2-butylene glycol on a left side and a larger amount of 1,3-butylene glycol on a right side. A vertical axis represents a sound velocity. As shown in FIG. 4, the sound velocity changed with the mixture ratio. When the mixture contained 100 wt % of 1,2-butylene glycol, the sound velocity was 1.45 km/s. The sound velocity increased with the ratio of 1,3-butylene glycol, and reached 1.54 km/s when the mixture contained 100 wt % of 1,3-butylene glycol. The sound velocity changed almost in simple proportion to the mixture ratio.

Since both 1,2-butylene glycol and 1,3-butylene glycol have a density of 1.0 kg/m$^3$, it is considered that the mixture has a density of 1.0 kg/m$^3$ regardless of the mixture ratio. Consequently, the acoustic impedance can be expressed as the product of the sound velocity shown in FIG. 4 and a density of 1.0 kg/m$^3$. As a result, it was confirmed that the acoustic impedance of the mixture was in a range of about 1.45 to 1.54 MRayl, and was similar to that of a living body with respect to any mixture ratio.

For example, the mixture containing 75 wt % of 1,3-butylene glycol, in other words 25 wt % of 1,2-butylene glycol had a sound velocity of 1.517 km/s. Accordingly, the acoustic impedance of this mixture was 1.517 MRayl, which was similar to that of a living body.

(2) Ultrasonic Attenuation

Figure 5:
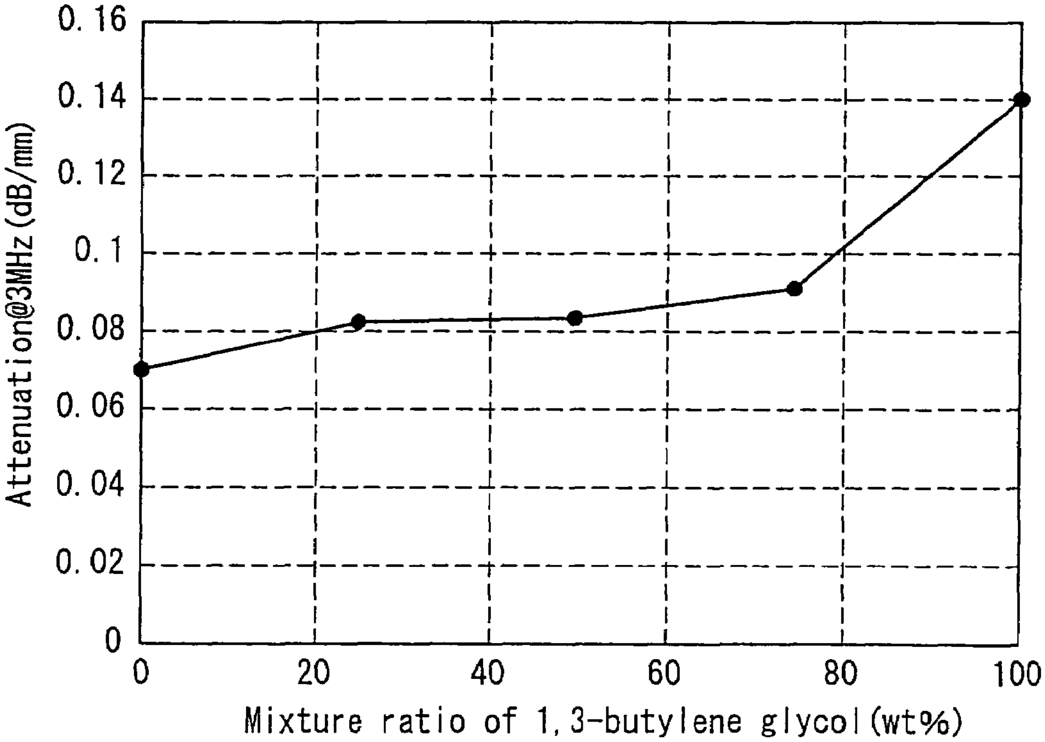
FIG. 5 is a graph showing the relationship between a mixture ratio and ultrasonic attenuation with respect to the mixture of 1,2-butylene glycol and 1,3-butylene glycol.

FIG. 5 is a graph showing ultrasonic attenuation at a frequency of 3 MHz when the mixture ratio (weight ratio) of the mixture of 1,2-butylene glycol and 1,3-butylene glycol is changed. The measurement of ultrasonic attenuation was performed in the same manner as described above.

In FIG. 5, a horizontal axis represents a mixture ratio, indicating that the mixture contains a larger amount of 1,2-butylene glycol on a left side and a larger amount of 1,3-butylene glycol on a right side, as in FIG. 4. A vertical axis represents an amount of attenuation. As shown in FIG. 5, the amount of attenuation increased with the content of 1,3-butylene glycol. Attenuation tended to increase eminently when the ratio of 1,3-butylene glycol exceeded 75 wt %, instead of changing in simple proportion to the mixture ratio of 1,3-butylene glycol. From this result, it was confirmed that when the content of 1,2-butylene glycol was not less than 25 wt %, the amount of attenuation was reduced considerably as compared with a conventional case of using only 1,3-butylene glycol, resulting in a further improvement in transmitting/receiving sensitivity for ultrasonic waves. For example, when the content of 1,2-butylene glycol was 25 wt % (the content of 1,3-butylene glycol was 75 wt %), the amount of attenuation was 0.091 dB/mm, which was about 35% smaller than an attenuation of 0.14 dB/mm obtained in the conventional case of using only 1,3-butylene glycol, and thus was highly useful.

As described above, in view of the acoustic impedance and ultrasonic attenuation, it is preferable that the content of 1,2-butylene glycol is in a range of 25 to 100 wt %. At this time, the mixture has an acoustic impedance of 1.45 to 1.517 MRayl, and produces an ultrasonic attenuation of 0.07 to 0.091 dB/mm (3 MHz).

(3) Viscosity

It is assumed that the viscosity of the mixture of 1,2-butylene glycol and 1,3-butylene glycol is between the viscosity of only 1,2-butylene glycol and the viscosity of only 1,3-butylene glycol.

(4) Other Characteristics

Both 1,2-butylene glycol and 1,3-butylene glycol are materials having only a very small effect on a living body. Also, these materials have only a very small adverse effect, such as corrosion, on the components such as the window formed of a plastic or the like, the ultrasonic transducing part formed of a piezoelectric ceramic or the like, and the drive shaft and the frame formed of metal or the like.

As described above, it was confirmed that the mixture of 1,2-butylene glycol and 1,3-butylene glycol also had favorable characteristics as the acoustic medium in terms of the acoustic characteristics, the viscosity, an effect (safety) on a living body, and an effect on the components.

In particular, when the mixture contains 25 to 100 wt % of 1,2-butylene glycol, the amount of ultrasonic attenuation is considerably small, whereby the transmitting/receiving sensitivity for ultrasonic waves can be improved significantly. Accordingly, with respect to the acoustic medium according to the present embodiment, the content of 1,2-butylene glycol in the mixture preferably is adjusted to 25 to 100 wt %.

In the present embodiment, although the mixture of 1,2-butylene glycol and 1,3-butylene glycol is used as the acoustic medium, the present invention is not limited thereto as mentioned above.

Further, the above description has been given taking as an example the case of using mechanical scanning in which the transducer is rotated by a motor. However, it is also possible to use electronic scanning by an array element in which a plurality of transducers are arranged in a strip shape.

INDUSTRIAL APPLICABILITY

The ultrasonic probe according to the present invention can transmit and receive ultrasonic waves with high sensitivity and can drive the ultrasonic transducing part smoothly at high speed. Therefore, it becomes possible to obtain a high-resolution three-dimensional ultrasonic image in real time. Consequently, this ultrasonic probe is useful for an ultrasonic diagnostic apparatus.

The invention claimed is:

1. An ultrasonic probe comprising: an ultrasonic transducing part for transmitting and receiving an ultrasonic wave; an outer case for storing the ultrasonic transducing part; and an acoustic medium charged in the outer case, wherein the acoustic medium contains only 1,2-butylene glycol or 1,2-butylene glycol and 1,3-butylene glycol.

2. The ultrasonic probe according to claim 1, wherein the acoustic medium contains only 1,2-butylene glycol.

3. The ultrasonic probe according to claim 1, wherein the acoustic medium contains 1,2-butylene glycol and 1,3-butylene glycol.

4. The ultrasonic probe according to claim 1, wherein the acoustic medium contains 25 to 100 wt % of 1,2-butylene glycol.

5. The ultrasonic probe according to claim 1, wherein the acoustic medium has an acoustic impedance of 1.45 to 1.517 MRayl at a temperature of 20° C., and produces an ultrasonic attenuation of 0.07 to 0.091 dB/mm at a frequency of 3 MHz.

6. The ultrasonic probe according to claim 1, comprising a mechanism for oscillating or rotating the ultrasonic transducing part.

7. The ultrasonic probe according to claim 1, wherein the ultrasonic transducing part includes an array element in which a plurality of transducers are arranged.

8. The ultrasonic probe according to claim 1, wherein the outer case includes an ultrasonic wave propagation window.

* * * * *